(12) United States Patent
Lazzara et al.

(10) Patent No.: US 6,565,357 B1
(45) Date of Patent: *May 20, 2003

(54) TWO-PIECE HEALING ABUTMENT SYSTEM

(75) Inventors: Richard J. Lazzara, Lake Worth, FL (US); Keith D. Beaty, Jupiter, FL (US); Curtis E. Jansen, Pacific Grove, CA (US)

(73) Assignee: Implant Innovations, Inc., Palm Beach Garden, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/659,505

(22) Filed: Sep. 11, 2000

Related U.S. Application Data

(63) Continuation of application No. 08/837,379, filed on Apr. 17, 1997, now Pat. No. 6,129,548, which is a division of application No. 08/527,508, filed on Sep. 13, 1995, now Pat. No. 5,674,071, which is a continuation of application No. 08/248,497, filed on May 24, 1994, now abandoned, which is a continuation of application No. 08/043,928, filed on Apr. 8, 1993, now Pat. No. 5,338,196.

(51) Int. Cl.$^7$ ................................................. A61C 3/00
(52) U.S. Cl. ........................................................ 433/173
(58) Field of Search ................................. 433/172, 173, 433/174, 175, 214

(56) References Cited

U.S. PATENT DOCUMENTS

| | | | |
|---|---|---|---|
| 4,086,701 A | 5/1978 | Kawahara et al. | 32/10 |
| 4,713,003 A * | 12/1987 | Symington et al. | 433/173 |
| 4,758,161 A | 7/1988 | Niznick | 433/173 |
| 4,790,753 A * | 12/1988 | Fradera | 433/174 |
| 4,842,518 A | 6/1989 | Linkow et al. | 433/174 |
| 4,850,870 A | 7/1989 | Lazzara et al. | 433/174 |
| 4,850,873 A | 7/1989 | Lazzara et al. | 433/220 |
| 4,856,994 A | 8/1989 | Lazzara et al. | 433/173 |
| 4,955,811 A | 9/1990 | Lazzara et al. | 433/173 |
| 4,988,298 A | 1/1991 | Lazzara et al. | 433/173 |

(List continued on next page.)

FOREIGN PATENT DOCUMENTS

| | | |
|---|---|---|
| EP | 0 442 855 A1 | 8/1991 |
| GB | 1291470 | 10/1972 |

OTHER PUBLICATIONS

Exhibit A, drawing of a healing abutment (no date).
Exhibit B, assembly drawing of a coping and the component drawings which comprise the coping assembly (no date).

(List continued on next page.)

Primary Examiner—John J. Wilson
(74) Attorney, Agent, or Firm—Jenkens & Gilchrist

(57) ABSTRACT

A two-piece healing abutment for forming an aperture in gingiva overlying an artificial root means installed in a jawbone of a patient's mouth is set forth. The root means has an upper end that is to be exposed in the aperture. The two-piece healing abutment comprises a first component and a second component. The first component has a transmucosal portion with an exterior surface for defining the aperture in the gingiva. The first component also has an internal bore extending therethrough and a lower end for engaging the upper end of the root means. The second component attached the first component on the root means. The second component extending through the bore of the first component and engaging the root means.

17 Claims, 2 Drawing Sheets

U.S. PATENT DOCUMENTS

| | | | |
|---|---|---|---|
| 5,000,685 A | 3/1991 | Brajnovic | 433/173 |
| 5,006,069 A | 4/1991 | Lazzara et al. | 433/173 |
| 5,015,186 A | 5/1991 | Detsch | 433/173 |
| 5,030,096 A | 7/1991 | Hurson et al. | 433/173 |
| 5,035,619 A | 7/1991 | Daftary | 433/173 |
| 5,040,983 A | 8/1991 | Binon | 433/173 |
| 5,071,351 A | 12/1991 | Green, Jr. et al. | 433/173 |
| 5,073,111 A | 12/1991 | Daftary | 433/173 |
| 5,100,323 A | 3/1992 | Friedman et al. | 433/173 |
| 5,106,300 A | 4/1992 | Voitik | 433/173 |
| 5,135,395 A | 8/1992 | Marlin | 433/174 |
| 5,145,371 A | 9/1992 | Jörnéus | 433/173 |
| 5,145,372 A | 9/1992 | Daftary et al. | 433/173 |
| 5,188,800 A | 2/1993 | Green, Jr. et al. | 422/23 |
| 5,209,659 A | 5/1993 | Friedman et al. | 433/173 |
| 5,209,666 A | 5/1993 | Balfour et al. | 433/173 |
| 5,213,502 A | 5/1993 | Daftary | 433/172 |
| 5,281,140 A | 1/1994 | Niznick | 433/172 |
| 5,292,252 A | 3/1994 | Nickerson et al. | 433/173 |
| 5,297,963 A | 3/1994 | Daftary | 433/172 |
| 5,312,254 A * | 5/1994 | Rosenlicht | 433/173 |
| 5,316,476 A * | 5/1994 | Krauser | 433/173 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,431,567 A | 7/1995 | Daftary | 433/172 |
| 5,433,606 A | 7/1995 | Niznick et al. | 433/173 |
| 5,547,377 A | 8/1996 | Daftary | 433/173 |
| 5,564,921 A | 10/1996 | Marlin | 433/172 |
| 5,662,476 A | 9/1997 | Ingber et al. | 433/213 |
| 5,674,073 A | 10/1997 | Ingber et al. | 433/213 |

OTHER PUBLICATIONS

Lewis, S. G., et al., *Single Tooth Implant Supported Restorations*, International Journal of Oral & Maxillofacial Implants, vol. 3, No. 1, pp. 25–30 (1988).

Lewis, S. G., et al., *The "UCLA" Abutment*, International Journal of Oral & Maxillofacial Implants, vol. 3, No. 3, pp. 183–189 (1988).

Perri, George DDS, et al., *Single Tooth Implants*, CDA Journal, vol. 17, No. 3 (Mar. 1989).

*The Anatomical Abutment System*, DIA™Dental Imaging Associates, Implanted—The Source (Oct. 9, 1991).

*Options For Oral Implantology . . . Oratronics Endosseous Tri–Demensional T–3D Oral Implant Healing System (OIHS)*, Oratronics, Inc. (1978).

Steri–Oss® Product Catalog (Feb. 1992).

Branemark System (Nobelpharma) Product Catalog Prosthetics (1991).

Steri–Oss® Product Catalog (Sep. 1990).

IMTEC Hexed–Head™Implant System Catalog (Spring 1993).

Interpore International, IMZ™Prosthetic Flow Chart (Jul. 1993).

Impla–Med Catalog (Mar. 1991).

Stryker Dental Implants Catalog Data Sheets (no date).

Stryker Dental Implants Price List (Jun. 1, 1993).

Deposition transcript of Dr. Fereidoun Daftary and exhibits (Aug. 21, 1998).

Documents produced by Dr. Fereidoun Daftary (FD2–498) (documents FD1, FD102–106, FD226, FD379, FD380 not in Applicants'possession due to claim of attorney/client privilege by Dr. Daftary) (various dates).

\* cited by examiner

TWO-PIECE HEALING ABUTMENT SYSTEM

This application is a continuation of U.S. application Ser. No. 08/837,379, filed Apr. 17, 1997, now U.S. Pat. No. 6,129,548, which is a divisional of application Ser. No. 08/527,508, filed Sep. 13, 1995, now U.S. Pat. No. 5,674,071, which is a file wrapper continuation of application Ser. No. 08/248,497, filed May 24, 1994, now abandoned, which is a continuation of application Ser. No. 08/043,928, filed Apr. 8, 1993, now U.S. Pat. No. 5,338,196.

BACKGROUND OF THE INVENTION

The field of restorative dentistry using artificial roots in the presently preferred form of osseointegrated cylinder shaped dental implants has progressed to the level where attention is now being given to providing restorations on them that closely replicate natural dentition in appearance, especially where the teeth emerge from the gums. The problems of achieving a natural locking emergence profile are addressed using a technique for fabricating implant supported restorations directly to an implant, employing custom wax patterns fashioned on abutment cylinders to achieve, for example, a custom made porcelain fused to metal restoration. This technique is described in published articles that appeared in The International Journal of Oral & Maxillofacial Implants, Vol. 3, Number 1, 1988 at pages 25–26 "Single Tooth Implant Supported Restorations" Lewis, S. G. et al., and Number 3, 1988 at pages 183–189 "The 'UCLA' Abutment", Lewis, S. G. et al. A similar result using a different abutment is described in U.S. Pat. No. 4,988,298, which is owned by the Assignee of the present invention. The problem is incompletely addressed in U.S. Pat. No. 5,073,111 issued to Daftary Dec. 17, 1991.

The dental restoration of a wholly or partially edentulous patient with dentition supported on dental implants is now frequently done in two stages. In the first stage the implant is placed and left to integrate with the jawbone. The second stage begins with re-accessing the implant through the gum and maintaining access with a healing cap or the like, and continues through the fabrication of restorative dentition in the laboratory using measurements and other information taken from time to time from the patient. During that time the patient may have only a healing cap is his or her mouth, or according to more recent and sophisticated procedures the patient may be fitted with temporary dentition from which additional refining measurements can be taken. Nevertheless, the healing abutments and the transfer copings, or pick up copings, of the prior art do not cooperate to provide room for making and installing on the implant an artificial tooth having an aesthetically pleasing or anatomically correct emergence profile. The gingival aspect of an implant is, typically not more than about 4.1 mm in diameter, whereas the longer (mesial-distal) dimension of a natural tooth where it emerges from the gum is between about 4.5 mm and about 8.0 mm. According to present practice, healing abutments, which are cylindrical in cross section, are chosen to approximate the mesial-distal dimension of the tooth being replaced. At the same time, the transfer copings, or pick up copings, of the prior art are all one size, about 4.5 mm in diameter. As a result, a gap is left in the gingiva, around the coping, and impression material fills this gap when an impression is taken. The gingiva also tend to collapse into this gap, resulting in less than accurate replication of the conditions in the patient's mouth. As a further consequence of these problems, it is difficult to make soft tissue models accurately. Stone models replicate these errors, and this requires technicians to shape the stone manually to comply with the conditions in the patient's mouth, or risk producing a crown with an inaccurate emergence profile or crown to abutment margin that is misplaced. These are severe problems, resulting from the fact that the designers of prior art components have thus far failed to recognize them. The present invention teaches new surgical and laboratory components, and new procedures, which eliminate such inaccurate and time wasting procedures, and improve the art of making anatomically correct and aesthetically pleasing dental restoration.

GENERAL NATURE OF THE INVENTION

In accordance with the present invention, a healing cap or healing abutment sized to maintain space for a desired emergence profile through the gum is used at the beginning of the second stage, in combination with an impression coping, or a pick up coping, having similar size specifications so that when the impression coping is fitted to the implant for taking the impression from which the stone model will be made the space for the desired emergence profile established in the gum by the healing abutment, or cap, will be preserved and replicated in the stone model, and in a soft tissue model, if desired. From such models restorative dentition can be fabricated without requiring the use of a specially contoured tooth support abutment as taught by Daftary, for example. Rather, artificial teeth replicating in all material respects the natural teeth that they replace can be fashioned on the model using components that have become standard in the art.

In one of its aspects the invention teaches a new method of preparing an aesthetically pleasing, as well as anatomically correct dental restoration on a natural or artificial root comprising first the step of preparing in the gingiva overlying the root an opening to the gingival aspect of the root, which opening is sufficient to accommodate the shape and contour of a natural tooth emerging through the gingiva from the root, followed by the step of making a rigid (e.g., stone) model that reproduces in stone or in overlying soft tissue exactly that opening and gingival aspect of the root, and then the step of forming on the model an artificial tooth that replicates in that opening the shape, size and contours desired in the restoration, and finally installing that restoration on the root. In another aspect, the invention provides a healing member (sometimes called a cap) that has a transmucosal section having at one end the subgingival cross sectional size and shape of the artificial root and where it emerges from the gingiva the mesial-distal size of the natural tooth being replaced, and means to attach that healing member non-rotatively to the root, for establishing the above mentioned opening in the gingiva. In another aspect, the invention provides a transfer coping for use in making the above mentioned rigid model having a transmucosal section that is substantially identical in cross sectioned size and shape to the transmucosal section of the healing member so as to fit fully within the opening in the gingiva that was formed by the healing member, and a supragingival section shaped for non-rotational embedment in resilient modelling material, together with means to attach the coping non-rotatively to the root. In still another aspect, the invention provides sets of matched pairs of healing members and transfer copings shaped and sized for use according to the invention to prepare restorations of particular types of teeth, such as molars, premolars, bicuspids, and incisors, as examples.

These and other features of the invention will be explained in greater detail in the following description of certain exemplary embodiments of the invention referring to the accompanying drawings in which.

DETAILED DESCRIPTION OF THE DRAWINGS

Figure 1:
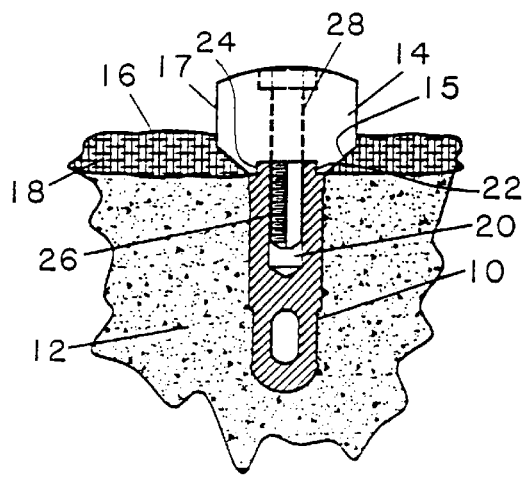
FIG. 1 is a longitudinal section that shows an implant installed in a bone with a healing cap in place.

FIG. 1 schematically illustrates a dental implant 10, of the osseointegrated type installed in a section of jawbone 12. The "second stage surgery" has begun, and a healing abutment 14 is in place on the implant. In order to provide for a more natural emergence profile in the final restoration, this abutment expands in a tapered transmucosal section 15 from the end contacting the implant toward an outer surface 16 of surrounding gingiva 18, beyond which walls 17 of the abutment extend vertically. As shown in FIG. 1, a portion of the vertical walls 17 is immersed in the gum tissue, below the outer surface 16, together with the tapered section 15. The implant has an internally threaded bore 20 axially located in it, surrounded at its gingival opening by a non-round boss 22, the external cross section of which typically is hexagonal. The healing abutment 14 has a corresponding non-round socket 24 enveloping the boss 22. In the illustrated embodiment through-bolt 25 passing through an axial bore 28 in the healing abutment is used to attach the abutment to the implant, in a well known manner. Attached in this manner, the healing abutment is not able to be rotated around the axis of the bolt. Healing abutments according to the invention may be prefabricated with a transmucosal section 15 having at the gingival surface 16 a round cross sectional shape the diameter of which is approximately equal to the mesial-distal dimension of the lost tooth being restored. Alternatively, the peripheral contour in the tapered section 15 may closely replicate the emergence profile of the natural tooth that was in the site where the implant 10 is installed. The invention contemplates providing sets of such prefabricated healing abutments, together with matching impression copings. The supragingival vertical walls of the healing abutment and the impression copings used with it may also be contoured to mimic the natural tooth cross-section, depending on the thickness of the gingiva 18 and the corresponding vertical dimension of the abutment.

Figure 2:
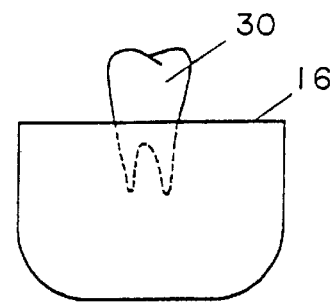
FIG. 2 shows a natural bicuspid.

FIG. 2 shows the general contours of a bicuspid 30 emerging from the outer surface 16 of the gingiva. A typical bicuspid is approximately 5.5 mm in mesial-distal dimension at the surface 16. A typical standard abutment or impression coping is at most 4.5 mm in diameter. Some teeth, e.g., molars, may be as much as 6.0 or 7.0 mm in mesial-distal dimension. Moreover, as appears in FIG. 6, which illustrates the cross section of an emergence profile 75 characteristic of an anterior tooth (not shown), it is also desirable to be able to provide for emergence profiles the cross sections of which do not even approximate round. To address these problems the invention provides methods and means to create and preserve openings in the gingiva 18 that are significantly larger than the cross section of the implant 10 and that may be round, or may have any desirable shape, and to preserve each such opening throughout the laboratory procedure for making and fitting the relevant dental restoration. Thus, as has been mentioned, the cross sectional shape of the transmucosal tapered portion 15 and the vertical wall portion 17 of the healing abutment may be round as long as its diameter approximates the mesial-distal size of the natural tooth.

Figure 3:
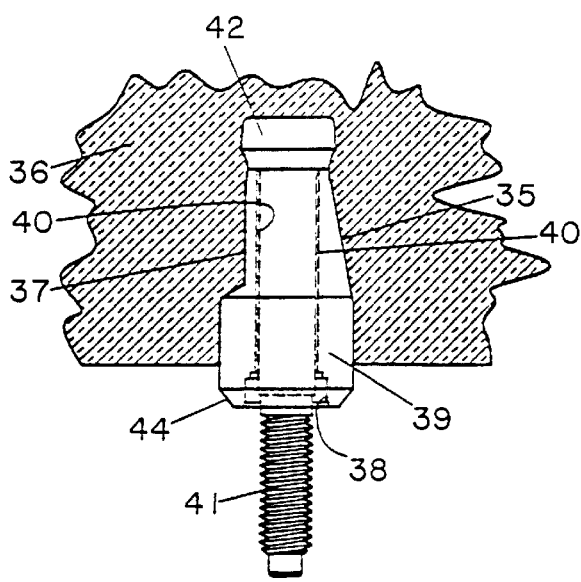
FIG. 3 is a longitudinal section that shows a transfer coping used to make an impression.

FIG. 3 shows a transfer coping 35 of a kind used to take impressions, buried in an impression material 36. The essential structure of this impression coping is described and claimed in U.S. Pat. No. 4,955,811, which is owned by the Assignee of the present invention. This impression coping has a flat surface 37 for locating it non-rotationally in the impression material, a hexagonal socket 38 in its base 39 for fixing it non-rotationally on the implant 10, an axial through bore 40 and a bolt 41 with an expanded head 42 for holding it in the impression material. The bolt 41 is used to attach the impression coping 35 to the implant 10. For the purposes of the present invention, the impression coping has a tapered section 44 at its end surrounding the socket 38 that replicates in size and shape the tapered transmucosal section 15 of the healing abutment 14. As shown in FIG. 3, a portion of the base 39 emerges from the impression material 36, together with the tapered section 44. The base 39 may also be contoured to mimic the natural cross section of the tooth being replaced, as its mentioned above.

Figure 4:
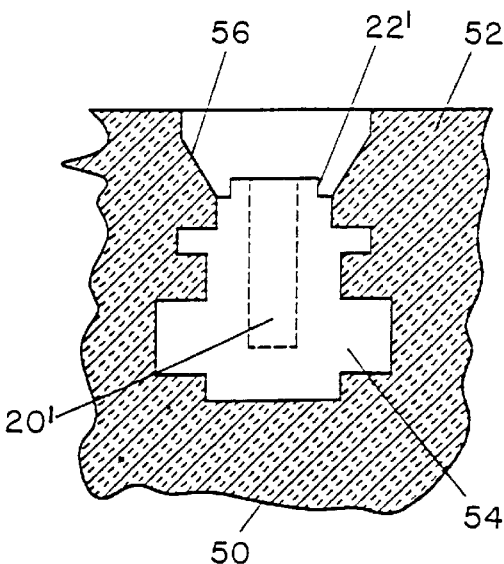
FIG. 4 is a longitudinal section that shows a stone model made from the impression.

FIG. 4 is a stone model 50 of the patient's implant installation site shown in FIG. 1. An implant replica 54 is encased in stone 52, according to well known dental laboratory practice. The replica 54 has a threaded bore 20' and a non-round boss 22' that are identical to the bore 20 and boss 22 of the implant 10. A tapered recess 56 in the surface of the stone surrounding the end of the replica 54 matches in size and shape the tapered section 44 and a part of the base 39 of the impression coping 35. Thus, the healing abutment fits equally well on the implant replica as on the implant.

The illustration in FIGS. 1,3, and 4 of a process in which the openings in the gingiva 18 and the model 50 have a "vertical" portion as well as the tapered portion is exemplary only, and is not intended to limit the invention to that feature.

Figure 5:
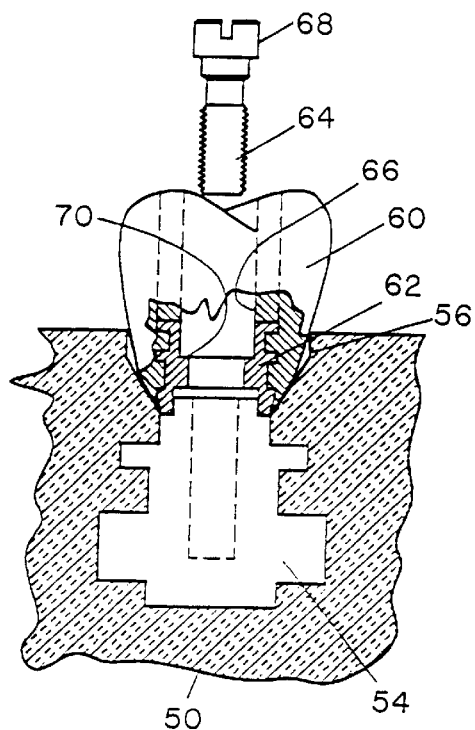
FIG. 5 shows the invention as used to replicate the natural tooth of FIG. 2.

An artificial bicuspid 60, as shown in FIG. 5, can be made with the aid of the model 50. A known form of core 62 is non-rotatively attachable to the implant replica with a screw bolt 64, passed through a through-bore 66 in the core. Head 68 of the bolt comes to rest on a shoulder 70 in the core 62, holding the core firmly attached to the implant replica 54 within the tapered recess 56. The artificial tooth is fashioned on the core using any available dental material such as porcelain or acrylic, for example. The dental material extends well within the tapered recess 56, so that outside this recess the core material cannot be seen. The core itself can be made of any suitable rigid material, such as titanium and its dilute alloys. After being fashioned and anatomically shaped as desired, the artificial tooth 60 can be transferred to the implant 10 and its appearance will be as is shown in FIG. 2. It will emerge from the gingiva 18 looking exactly the same as a natural tooth. According to well known dental practice, the opening into the core at the top of the tooth 60 will be filled with a suitable dental cement or the like, and polished so as to be for all practical purposes not distinguishable from the rest of the tooth. The above mentioned U.S. Pat. No. 4,988,298 illustrates an artificial tooth that can benefit from the invention.

Figure 6:
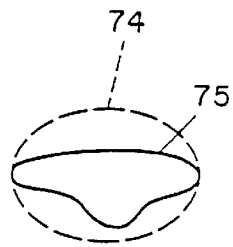
FIG. 6 shows the cross section of a natural emergence profile that the invention can replicate.

Because the component parts used in this invention can be made so that they are non-rotatably attachable together, it is not necessary that they be cylindrical in cross section where they are attachable one to the other. Thus, the healing abutment 14, the base 39 of the impression coping 35, and the subgingival section of the artificial tooth 60 can each be given the same cross sectional size and shape, changing gradually from round at the subgingival aspect of the implant fixture 10 to non-round proceeding toward the gingival surface through which the artificial tooth will emerge from the surface 16 of the overlying gingiva. In this manner that size and shape can initially be established by the healing abutment in the opening through the gingiva 18, and the same size and shape in the correct orientation around the axis of the implant 10 can be replicated and preserved in the model 50, thereby enabling the tooth 60 to be formed in the laboratory with the correct emergence profile. This feature of the invention is particularly advantageous when restoring anterior dentition, where the emergence cross section, e.g., 75 as is indicated in FIG. 6, has segments that are almost straight, and curved segments that turn on short radii.

The invention is not limited to the use of non-rotatively attachable components. In its more general aspects, the invention contemplates providing transmucosal openings that may be round with a diameter that approximates the mesial-distal dimension of the missing tooth that is being replaced, and preserving that dimension in a round opening throughout the laboratory procedure. This simple arrangement provides the basic advantages of the invention, which include eliminating the need to surgically expand a trans-tissue opening that was originally, or has become, too small to receive the restoration, and eliminating the need for laboratory technicians to hand finish stone models in which the trans-tissue opening was incorrectly formed due to causes that are mentioned above. Provided the trans-tissue opening is formed and maintained large enough to receive the restoration, last minute surgery is not needed, and the tissue will grow to the restoration. Referring to FIG. 6, dashed line circle 74 represents a trans-tissue opening that is larger than the tooth 75. In this situation, there is no need to provide the non-rotative features such as the mating non-round boss 22 and socket 24.

According to the invention, healing abutments 14 and transfer copings 35 may be prefabricated in sets of pairs, each pair having an "emergence profile contour" that is representative of a range of teeth of a particular type; that is, for example, large molars, small molars, premolars, bicuspids, and anterior incisors. The restorative dentist may then choose a pair that most closely replicates the emergence profile that is desired, modify the members of that pair if such is deemed necessary or desirable, and then make a restoration in accordance with the present invention that will be aesthetically pleasing and very close to anatomically correct.

Figure 7:
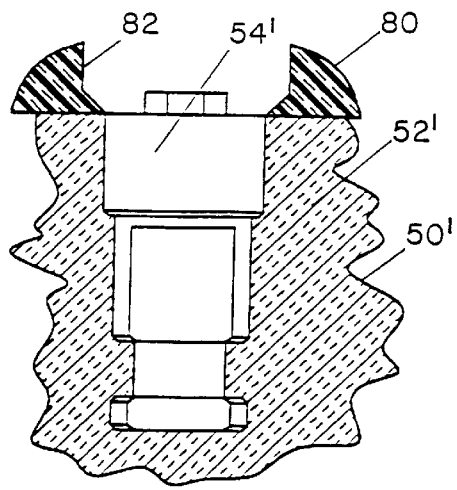
FIG. 7 is a cross section that shows a soft tissue model.

FIG. 7 shows a stone model 50' similar to the model 50 of FIG. 4, but in cross section rather than in longitudinal section, and including a stone foundation 52' rigidly holding an implant replica 54'. A soft tissue layer 80, which replicates the human gingiva 18, overlies the stone part. This layer can be made of any suitable plastics or rubber-like material having physical properties such as softness and elasticity that resemble the physical properties of human gum tissue. Certain silicone based rubber and plastics materials are suitable, preference being given to those that can be fabricated from a soft flowable state. In use, the soft flowable plastics material is placed in the impression around the tapered section 44 and emerging portion of the base 39 of the transfer coping 35 to a thickness the same as that of the patient's gingiva 18. The resulting opening 82 is similar to the opening 56 in the stone that is shown in FIG. 4. It has the advantage that the laboratory technician can manipulate the model exactly as the dentist manipulates the patient's gingiva.

Figure 8:
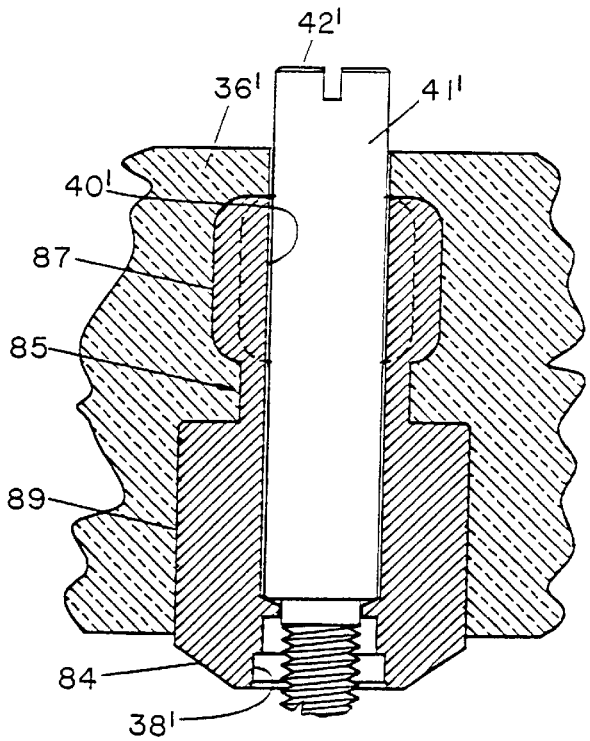
FIG. 8 shows a pick up coping used to make an impression.

FIG. 8 shows a pick-up coping 85 buried in an impression material 36'. This impression coping has a non-round head portion 87 for anchoring the coping non-rotationally on the implant, if desired, an axial through bore 40' and a bolt 41' passing through this bore to attach the impression coping to the implant. The proximal end 42' of the bolt has no expanded head on it for the reason that in use when an impression is taken, this end of the bolt extends through a hole in the impression tray (not shown) and, when the impression material has set up in the tray the bolt 41' is unscrewed from the implant by accessing its proximal end 42' from the outside, the tray and the coping 85 remains in (is "picked up" by) the impression material, being anchored therein by its expanded head 87. For the purpose of this invention, the pick up coping 85 functions like the transfer coping 35 of FIG. 3. Thus, the base 89 is expanded to a diameter that approximates the mesial-distal dimension of the natural tooth that is being restored and tapered section 84 reduces subgingivally to the diameter of the implant or other underlying support that may be present. Like the base 39 in FIG. 3, the base 89 may be contoured to mimic the cross section of the natural tooth.

What is claimed is:

1. A method for making a model of a site in a mouth of a patient by use of a kit of impression copings, said site containing a dental implant in a jawbone and gingiva overlying said jawbone, said method comprising:

forming an opening in said overlying gingiva with a gingival healing component that is attached to said dental implant, said gingival healing component being a distinct component from said kit of impression copings, said opening corresponding to a contour of a gingival healing component;

removing said gingival healing component from said implant;

selecting one of said impression copings that has dimensions corresponding to said opening, each of said impression copings in said kit including a transgingival section having a round cross-sectional shape and a lower end for engaging said dental implant, a supragingival section adapted for embedment in a resilient impression material and being integral with said transgingival section, wherein said transgingival section of a first impression coping has a different dimension than a transgingival section of a second impression coping allowing for the selection of a particular impression coping corresponding to a particular dimension of said opening in said gingiva, said lower end of said first impression coping being substantially similar to said lower end of said second impression coping for mating with said dental implant; and attaching said selected one of said impression copings to said implant.

2. The method of claim 1, wherein said attaching includes using a screw to hold said impression coping on said implant.

3. The method of claim 2, wherein said screw has a head portion that is wider than an upper end of said supragingival section.

4. The method of claim 1, wherein said supragingival section is narrower than said transgingival section.

5. The method of claim 1, wherein each of said impression copings is a transfer-type impression coping that remains on said implant after said resilient material has been removed.

6. The method of claim 1, wherein said supragingival section has a non-symmetrical cross-section.

7. The method of claim 1, further including selecting said gingival healing component from a kit of gingival healing components having different dimensions.

8. The method of claim 1, wherein said implant and said impression copings have mating non-round fittings.

9. The method of claim 8, wherein said non-round fitting of said implant is a hexagonal boss and said non-round fittings of said impression copings are hexagonal sockets.

10. A method for developing an aperture through gingiva overlying jawbone, said method comprising:

installing an implant in said jawbone;

after said installing, attaching a healing abutment to said implant, said healing abutment including a member having a lower surface for engaging said implant and an exterior wall for engaging said overlying gingiva and forming said aperture through said overlying gingiva, said exterior wall includes an outwardly tapering portion between said lower surface and an upper surface of said member, said exterior wall being smooth and lacking any discontinuities that define an indentation, said member having a bore extending therethrough, said attaching including passing a threaded stem of a screw through said bore to engage a threaded bore of said implant, said screw having a head which does not protrude above said upper surface of said member, said head and said upper surface of said member together forming an exposed uppermost region of said healing abutment; and while said exposed uppermost region is above said gingiva, allowing said gingiva to heal around said healing abutment to form said aperture.

11. The method of claim 10, wherein said tapering portion is immediately adjacent to said lower surface.

12. The method of claim 11, wherein said exterior wall includes a generally cylindrical portion above tapering portion.

13. The method of claim 10, wherein said implant and said healing abutment have mating non-round fittings, said attaching including engaging said mating non-round fittings.

14. The method of claim 13, wherein said non-round fitting of said implant is hexagonal boss and said non-round fitting of said healing abutment is a hexagonal socket.

15. A method for developing an aperture through gingiva overlying jawbone, said method comprising:

installing an implant in said jawbone;

after said installing, attaching a healing abutment to said implant, said healing abutment including a member with an external side surface for forming an aperture in said overlying gingiva and an internal surface defining a bore extending through said member, said external surface terminating in an upper surface, said member having a lower surface having a dimension, all transverse dimensions of said exterior side surface being substantially the same as or greater than said dimension of said lower surface; said attaching including passing a screw through said bore and threading said screw into a threaded bore of said implant to hold said member on said implant, said screw having a head that, together with said upper surface of said member, forms an exposed uppermost region of said healing abutment; and while said exposed uppermost region is above said gingiva, allowing said gingiva to heal around said healing abutment to form said aperture.

16. The method of claim 15, wherein said external side surface includes a generally conical lower region and a generally cylindrical upper region.

17. The method of claim 15, wherein said implant and said healing abutment have mating non-round fittings, said attaching including engaging said mating non-round fittings.

* * * * *